US012617768B2

(12) United States Patent
Ametamey et al.

(10) Patent No.: US 12,617,768 B2
(45) **Date of Patent: *May 5, 2026**

(54) RADIOLABELED CANNABINOID RECEPTOR 2 LIGAND

(71) Applicants: HOFFMANN-LA ROCHE INC., Little Falls, NJ (US); ETH ZUERICH, Zurich (CH)

(72) Inventors: Simon M. Ametamey, Zurich (CH); Luca Gobbi, Basel (CH); Uwe Grether, Basel (CH); Julian Kretz, Basel (CH); Dieter Muri, Basel (CH); Ahmed Haider Wahauib, Zurich (CH)

(73) Assignees: HOFFMANN-LA ROCHE INC., Little Falls, NJ (US); ETH ZUERICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/670,587

(22) Filed: May 21, 2024

(65) Prior Publication Data

US 2024/0308974 A1 Sep. 19, 2024

Related U.S. Application Data

(63) Continuation of application No. 17/125,655, filed on Dec. 17, 2020, now Pat. No. 11,999,710, which is a continuation of application No. PCT/EP2019/066799, filed on Jun. 25, 2019.

(30) Foreign Application Priority Data

Jun. 27, 2018 (EP) .................................... 18180154

(51) Int. Cl.
*C07D 401/04* (2006.01)
*C07B 59/00* (2006.01)

(52) U.S. Cl.
CPC .......... *C07D 401/04* (2013.01); *C07B 59/002* (2013.01); *C07B 2200/05* (2013.01)

(58) Field of Classification Search
CPC .. C07D 401/04; C07B 59/002; C07B 2200/05
USPC ........................................................ 424/1.89
See application file for complete search history.

(56) References Cited

U.S. PATENT DOCUMENTS

| | | | |
|---|---|---|---|
| 9,303,012 | B2 | 4/2016 | Bendels et al. |
| 9,321,727 | B2 | 4/2016 | Bissantz et al. |
| 9,403,808 | B2 | 8/2016 | Bissantz et al. |
| 9,409,866 | B2 | 8/2016 | Grether et al. |
| 9,512,141 | B2 | 12/2016 | Dhurwasulu et al. |
| 9,522,886 | B2 | 12/2016 | Frei et al. |
| 10,155,942 | B2 | 12/2018 | Kurihara et al. |
| 10,308,659 | B2 | 6/2019 | Gavelle et al. |
| 10,912,849 | B2 | 2/2021 | Wu et al. |
| 11,479,807 | B2 | 10/2022 | Kennedy et al. |
| 11,655,243 | B2 | 5/2023 | Ametamey et al. |
| 11,999,710 | B2 | 6/2024 | Ametamey et al. |
| 12,071,420 | B2 | 8/2024 | Gobbi et al. |
| 2005/0245544 | A1 | 11/2005 | Bell et al. |
| 2007/0105861 | A1 | 5/2007 | Lee et al. |
| 2008/0280868 | A1 | 11/2008 | Eatherton et al. |
| 2018/0344882 | A1 | 12/2018 | Wu et al. |
| 2020/0182940 | A1 | 6/2020 | Tsai |
| 2020/0239490 | A1 | 7/2020 | Frei et al. |
| 2021/0115011 | A1 | 4/2021 | Gobbi et al. |
| 2021/0115012 | A1 | 4/2021 | Ametamey et al. |
| 2021/0115027 | A1 | 4/2021 | Ametamey et al. |
| 2021/0130334 | A1 | 5/2021 | Ametamey et al. |

FOREIGN PATENT DOCUMENTS

| | | | |
|---|---|---|---|
| CL | 2020002927 | A1 | 3/2021 |
| CN | 1703402 | A | 11/2005 |
| CN | 101522644 | A | 9/2009 |
| CN | 103608332 | A | 2/2014 |
| CN | 104024232 | A | 9/2014 |
| CN | 104837830 | A | 8/2015 |
| CN | 104854092 | A | 8/2015 |
| CN | 106132958 | A | 11/2016 |

(Continued)

OTHER PUBLICATIONS

GW405833 hydrochloride, CAS No. 180002-83-9, retrieved from https://www.sigmaaldrich.com/IN/en/search/180002-83-9?focus=products&page=1&perpage=30&sort=relevance&term=180002-83-9&type=cas_number, Retrieved on Jun. 12, 2024, 2 pages.

(Continued)

*Primary Examiner* — Michael G. Hartley
*Assistant Examiner* — Sean R Donohue
(74) *Attorney, Agent, or Firm* — Mintz, Levin, Cohn, Ferris, Glovsky and Popeo, P.C.

(57) ABSTRACT

The present invention relates to a compound of formula (I)

(I)

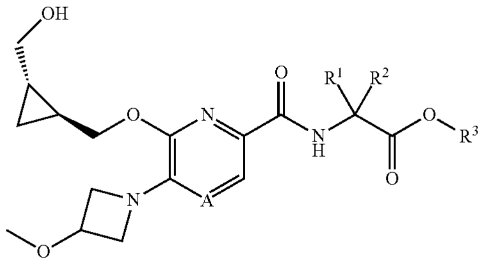

wherein $R^1$, $R^2$, and $R^3$ are defined as in the description and in the claims. The compound of formula (I) can be used as a radiolabeled ligand.

10 Claims, 1 Drawing Sheet

(56) References Cited

FOREIGN PATENT DOCUMENTS

| | | | |
|---|---|---|---|
| CN | 106349156 | A | 1/2017 |
| CN | 106458984 | A | 2/2017 |
| CO | 6890101 | A2 | 3/2014 |
| CO | 2017005374 | A | 8/2017 |
| ES | 2388833 | T3 | 10/2012 |
| JP | 2014516071 | A | 7/2014 |
| JP | 2014534210 | A | 12/2014 |
| JP | 2016501240 | A | 1/2016 |
| JP | 2017509688 | A | 4/2017 |
| JP | 2017534580 | A | 11/2017 |
| JP | 2021528455 | A | 10/2021 |
| JP | 2022501311 | A | 1/2022 |
| RU | 2612138 | C2 | 3/2017 |
| WO | 9504045 | A1 | 2/1995 |
| WO | 2012168350 | A1 | 12/2012 |
| WO | 2013060751 | A1 | 5/2013 |
| WO | 2014086705 | A1 | 6/2014 |
| WO | 2014086805 | A1 | 6/2014 |
| WO | 2014086806 | A1 | 6/2014 |
| WO | 2014086807 | A1 | 6/2014 |
| WO | 2014154612 | A1 | 10/2014 |
| WO | 2015150438 | A1 | 10/2015 |
| WO | 2015150440 | A1 | 10/2015 |
| WO | 2016066534 | A1 | 5/2016 |
| WO | 2017097732 | A1 | 6/2017 |
| WO | 2018234284 | A1 | 12/2018 |
| WO | 2020002270 | A1 | 1/2020 |
| WO | 2020002314 | A1 | 1/2020 |
| WO | 2020002320 | A1 | 1/2020 |

OTHER PUBLICATIONS

Akhmetshina et al. (Apr. 2009) "The Cannabinoid Receptor CB2 Exerts Antifibrotic Effects in Experimental Dermal Fibrosis", Arthritis & Rheumatology, 60(4):1129-1136.
Bab et al. (Jan. 2008) "Cannabinoid Receptors and the Regulation of Bone Mass", British Journal of Pharmacology, 153(2):182-188.
Batkai et al. (Jun. 2007) "Cannabinoid-2 Receptor Mediates Protection Against Hepatic Ischemia/reperfusion Injury", The FASEB Journal, 21(8):1788-1800.
Beltramo, Massimiliano (Jan. 2009) "Cannabinoid Type 2 Receptor as a Target for Chronic—Pain", Mini-Reviews in Medicinal Chemistry, 9(1):11-25.
Cabral et al. (Dec. 2005) "Cannabinoid Receptors in Microglia of the Central Nervous System: Immune Functional Relevance", Journal of Leukocyte Biology, 78(6):1192-1197.
Caille et al. (Nov. 6, 2017) "From Structure-Activity Relationships on Thiazole Derivatives to the In Vivo Evaluation of a New Radiotracer for Cannabinoid Subtype 2 PET Imaging", Molecular Pharmaceutics, 14(11):4064-4078 (30 pages).
Defer et al. (Jul. 2009) "The Cannabinoid Receptor Type 2 Promotes Cardiac Myocyte and Fibroblast Survival and Protects Against Ischemia/reperfusion-induced Cardiomyopathy", The FASEB Journal, 23(7):2120-2130.
Feizi et al., "The Preventive Effect of Cannabinoids on Reperfusion-induced Ischemia of Mouse Kidney", Experimental and Toxicologic Pathology, Aug. 2008, 60(4-5):405-410.
Garcia-Gonzalez et al. (Sep. 2009) "Cannabinoids Inhibit Fibrogenesis in Diffuse Systemic Sclerosis Fibroblasts", Rheumatology, 48(9):1050-1056.
Julien et al. (Mar. 2005) "Antifibrogenic Role of the Cannabinoid Receptor CB2 in the Liver", Gastroenterology, 128(3):742-755.
Lotersztajn et al. (Mar. 2007) "Endocannabinoids: Therapeutic Perspectives in Chronic Liver Diseases", Gastroentérologie Clinique et Biologique, 31(3):255-258.
Mach et al. (May 2008) "The Role of the Endocannabinoid System in Atherosclerosis", Journal of Neuroendocrinology, 20 Suppl 1:53-57.
Mallat et al. (Mar. 2007) "Cannabinoid Receptors as New Targets of Antifibrosing Strategies During Chronic Liver Diseases", Expert Opinion on Therapeutic Targets, 11(3):403-409.
Moldovan et al. (Sep. 8, 2016) "Development of a High-Affinity PET Radioligand for Imaging Cannabinoid Subtype 2 Receptor", Journal of Medicinal Chemistry, 59(17):7840-7855.
Muller et al. (Sep. 28, 2007) "Fluorine in Pharmaceuticals: Looking Beyond Intuition", Science, 317 (5846):1881-1886.
Munoz-Luque (Feb. 2008) "Regression of Fibrosis After Chronic Stimulation of Cannabinoid CB2 Receptor in Cirrhotic Rats", Journal of Pharmacology and Experimental Therapeutics, 324(2):475-483.
Pacher et al. (Jan. 2008) "Endocannabinoids and Cannabinoid Receptors in Ischaemia-reperfusion Injury and Preconditioning", British Journal of Pharmacology, 153(2):252-262.
Yang et al. (May 2009) "Inhibition of Hepatic Tumour Necrosis Factor-alpha Attenuates the Anandamide-induced Vasoconstrictive Response in Cirrhotic Rat Livers", Liver International, 29(5):678-685.
Zhang et al. (Jul. 2007) "Cannabinoid CB(2) Receptor Activation Decreases Cerebral Infarction in a Mouse Focal Ischemia/reperfusion Model", Journal of Cerebral Blood Flow & Metabolism, 27(7):1387-1396.
Lotersztajn et al. (Jan. 2008) "CB2 Receptors as New Therapeutic Targets for Liver Diseases", British Journal of Pharmacology, 153(2):286-289.
Communication Pursuant to Article 94(3) EPC for European Application No. 19733484.0, mailed on Sep. 23, 2022, 6 pages.
International Search Report and Written Opinion for International Application No. PCT/EP2019/066799, mailed on Jul. 10, 2019, 11 pages.
International Search Report and Written Opinion issued in International Application No. PCT/EP2019/066811, mailed on Aug. 8, 2019, 10 pages.
Search Report for Russian Application No. 2021101106/04(002123), mailed on Aug. 23, 2022, 2 pages.
Belikov, V.G. (2007) "Pharmaceutical Chemistry", Moscow: MEDpress-Inform, 13 pages.
Haider et al. (2020) "Identification and Preclinical Development of a 2,5,6-Trisubstituted Fluorinated Pyridine Derivative as a Radioligand for the Positron Emission Tomography Imaging of Cannabinoid Type 2 Receptors", Journal of Medicinal Chemistry, 63(18):10287-10306.
Haider et al. (2019) "Structure-Activity Relationship Studies of Pyridine-Based Ligands and Identification of a Fluorinated Derivative for Positron Emission Tomography Imaging of Cannabinoid Type 2 Receptors", Journal of Medicinal Chemistry, 62(24):11165-11181.
Pacher et al. (2011) "Is Lipid Signaling Through Cannabinoid 2 Receptors Part of a Protective System?", Progress in lipid research, 50(2):193-211.
Pitt et al. (1975) "The Synthesis of Deuterium, Carbon-14, and Carrier-free Tritium Labeled Cannabinoids", Journal of Labelled Compounds, 11(4):551-575.
Slavik et al. (May 7, 2015) "Discovery of a High Affinity and Selective Pyridine Analog as a Potential Positron Emission Tomography Imaging Agent for Cannabinoid Type 2 Receptor", Journal of Medicinal Chemistry, 58(10):4266-4277.

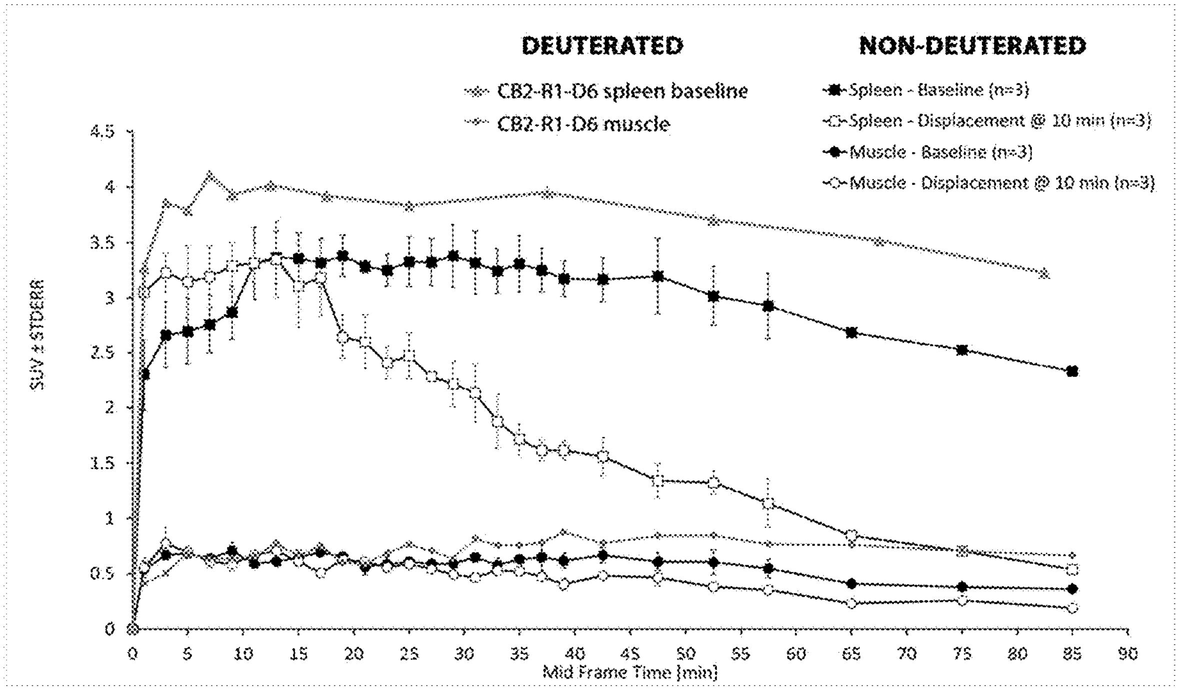
DEUTERATED
CB2-R1-D6 spleen baseline
CB2-R1-D6 muscle
NON-DEUTERATED
Spleen - Baseline (n=3)
Spleen - Displacement @ 10 min (n=3)
Muscle - Baseline (n=3)
Muscle - Displacement @ 10 min (n=3)
SUV ± STDERR
Mid Frame Time (min)
0
0.5
1
1.5
2
2.5
3
3.5
4
4.5
0 5 10 15 20 25 30 35 40 45 50 55 60 65 70 75 80 85 90

RADIOLABELED CANNABINOID RECEPTOR 2 LIGAND

CROSS-REFERENCE TO RELATED APPLICATIONS

This application is a continuation of U.S. application Ser. No. 17/125,655 filed Dec. 17, 2020, issued as U.S. Pat. No. 11,999,710, which is a continuation of International Application No. PCT/EP2019/066799 having an International Filing Date of 25 Jun. 2019, which claims the benefit of priority to European Patent Application No. 18180154.9, filed 27 Jun. 2018, the contents of which applications are hereby incorporated by reference in their entirety.

The present invention relates to a radiolabeled Cannabinoid Receptor 2 ligand. The invention relates in particular to a compound of formula (I):

(I)

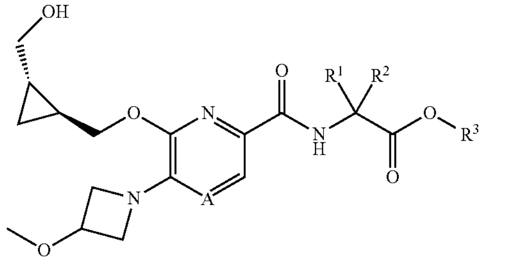

wherein $R^1$ and $R^2$ are both ethyl at the same time; and $R^3$ is 3-fluoropropyl;

provided that at least one of $R^1$, $R^2$ and $R^3$ comprises at least one radionuclide;

or a pharmaceutically acceptable salt thereof.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor has a wide range of expression. It is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages, B- and, T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also present in the brain where it is found primarily on microglia and not on neurons (Cabral, G. A. et al. Br J Pharmacol 2008, 153(2), 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6) and liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factors) generated in the remote organ or tissue enters the blood stream and activates its respective receptor in the target tissue thereby recruiting the various intracellular pathways of cardioprotection implicated in ischemic preconditioning.

Recent data indicate that endocannabinoids and their receptors, in particular CB2, might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in a sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of the CB2 receptor by selective CB2 agonists has in fact been shown to exert an anti-fibrotic effect in diffuse systemic sclerosis (Garcia-Gonzalez, E. et al. Rheumatology (Oxford) 2009, 48(9), 1050-6) and the CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The need to unequivocally detect CB2 in tissues came along with the growing interest in this receptor. Assessing CB2 expression and receptor occupancy in patients or samples with appropriate tools could verify the target cell of expression, permit dose finding of any CB2 ligand in human studies, or be used for diagnostic purpose.

There is up to now a deficit in efficient tools for the detection of the CB2 receptor protein in tissues, which is a consequence of the low expression levels of the CB2 receptor. Another reason for the lack of specific antibodies as detection tools of CB2 could be derived from the apparent difficulty to use CB2 as an immunogen.

A number of PET tracers targeting the CB2 receptor where described in the most recent years (Caillé, F et al., Mol. Pharmaceutics, 2017, 14 (11), 4064-4078 and references mentioned in there). All of these are labelled with the short-lived radioisotope $^{11}C$ (decay half-life 20.3 min), or lack selectivity versus the CB1 receptor and are suffering of high lipophilicity, leading to an unfavorable signal-to-noise ratio. A novel PET tracer with high selectivity and specificity for CB2 and containing a $^{18}F$ label would be highly desirable. In particular the longer lived $^{18}F$ isotope (decay half-life 110 min) would greatly facilitate distribution and use of the tracer after its production. In addition the low positron emission energy of $^{18}F$ makes this isotope the preferred PET radionuclide for obtaining images with higher spatial resolution.

Incorporation of a fluorine atom in a small molecule chemical structure has a profound effect on its physicochemical and biological properties (K. Müller et al, 2007, 317 (5846), 1881-1886). When searching for a PET tracer candidate structure ameanable to radiofluorination, is thus not evident to identify appropriate compounds maintaining and combining all desired properties in one molecule.

The compound of formula (I) as defined above was surprisingly identified to have the desired properties and was found to possess highly reduced non-specific binding.

The compound of formula (I) proved to specifically and selectively bind to membranes prepared from cells recombinantly expressing CB2 receptors. Furthermore, the compound of formula (I) turned out to specifically label CB2 receptors in spleen tissues, which is an organ with a high expression of both CB1 and CB2 receptors. Moreover, in spleen tissues isolated from CB2 receptor deficient mice, binding by the compound of formula (I) was absent. In this particular case, the total binding signal could not be reduced by excess of unlabeled ($R^1$=$CH_3$) compound of formula (I).

The compound of formula (I) can therefore be used for example in tissue autoradiography and PET imaging, e.g. to assess receptor expression and receptor occupancy, for dose finding of any CB2 ligand in human studies, or for diagnostic purposes.

In the present description, the term "radionuclide" defines the isotope of an atom with an unstable nucleus and that undergoes radioactive decay. Particular radionuclides of the invention are [$^3$H], [$^{18}$F], [$^{11}$C] and [$^{14}$C], more particularly [$^3$H] and [$^{18}$F].

The term "binding constant" refers to the equilibrium constant associated with the binding reaction of a ligand to a receptor.

The term "selective binding" characterizes the binding of a ligand to a very limited type of receptors.

The invention thus relates to:

A compound of formula (I) wherein A is CH;

A compound of formula (I) wherein both $R^1$ and $R^2$ comprise at least one radionuclide or $R^3$ comprises a radionuclide;

A compound of formula (I) wherein the at least one radionuclide is independently selected from [$^3$H], [$^{18}$F] and [$^{11}$C];

A compound of formula (I) wherein $R^1$ and $R^2$ are both —$C^3HH$—$C^3HH_2$ at the same time;

A compound of formula (I) wherein $R^3$ is —$CH_2$—$CH_2$—$CH_2{}^{18}F$ or —$CD_2$-$CD_2$-$CD_2{}^{18}F$;

A compound of formula (I) selected from 3-[$^{18}$F]Fluoranylpropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate;

(1,1,2,2,3,3-Hexadeuterio-3-[$^{18}$F]fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate; and 3-Fluoropropyl 2-(1,2-ditritioethyl)-2-[[6-[[(1S,2S)-2-(hydroxymethyl)cyclopropyl]methoxy]-5-(3-methoxyazetidin-1-yl)pyridine-2-carbonyl]amino]-3,4-ditritio-butanoate;

or a pharmaceutically acceptable salt thereof;

The use of a compound of formula (I) for localizing a CB2 receptor in a patient, an animal or a sample.

The use of a compound of formula (I) for imaging a CB2 receptor in a patient, an animal or sample.

The use of a compound of formula (I) for determining whether another compound binds to a CB2 receptor.

The use of a compound of formula (I) for determining whether another compound binds to a CB2 receptor further comprising measuring the binding constant of said another compound to the CB2 receptor.

The use of a compound of formula (I) for determining whether another compound binds in vivo to a CB2 receptor by means of a receptor occupancy study with PET.

The use as defined above in the presence of the CB1 receptor.

The use of a compound of formula (I) to determine whether a disease is characterized by a change in the expression of the CB2 receptor;

The use of a compound of formula (I) to determine whether a disease is characterized by a change in the expression of the CB2 receptor, wherein the disease is pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for use in the diagnosis in a patient or tissue of a disease.

A compound of formula (I) for use in the diagnosis in a patient or tissue of a disease as defined above, wherein the disease is characterized by a change in the expression of the CB2 receptor in said patient or tissue compared to the expression of the CB2 receptors in a healthy subject or tissue.

A compound for use as defined above wherein the diagnosis comprises the step of comparing the expression of the CB2 receptor in the patient or tissue to the expression of the CB2 receptor in a healthy subject or tissue.

The use of a compound of formula (I) to predict whether a patient affected with a disease is likely to respond to a treatment involving the administration of a CB2 ligand.

The use of a compound of formula (I) to predict whether a patient affected with a disease is likely to respond to a treatment involving the administration of a CB2 ligand comprising comparing the expression of the CB2 receptor in the patient to the expression of the CB2 receptor in a healthy subject or tissue.

The use of a compound of formula (I) to assess the efficacy of a medical therapy in a patient, comprising monitoring the CB2 receptor density (i.e. the CB2 receptor expression) in the patient before, during and/or after said medical therapy.

The use of a compound of formula (I) for determining the dose of a CB2 ligand that needs to be administered to a patient in need thereof.

The invention further relates to a method for identifying a compound that binds to a CB2 receptor comprising the following steps:

(a) contacting the compound suspected to bind to the CB2 receptor with a sample comprising a CB2 receptor and a compound of formula (I); and
(b) monitoring whether the compound suspected to bind to the CB2 receptor influences the binding of the compound of formula (I) to the CB2 receptor.

The invention also relates to a method as defined above, further comprising the step of measuring the binding strength to the CB2 receptor of the compound suspected to bind to the CB2 receptor.

The invention also relates to a method for identifying a cellular receptor as a CB2 receptor comprising the following steps:

(a) contacting a sample suspected to comprise a CB2 receptor with a compound of formula (I); and
(b) monitoring whether the binding of the compound of formula (I) has occurred; and
(c) optionally further contacting the sample with another known CB2 ligand and monitoring whether said known CB2 ligand has displaced the compound of formula (I) from its binding site.

The invention also relates to a method for measuring in a sample the percentage of CB2 receptors occupied by a compound suspected to bind to the CB2 receptor when said compound is put in contact with the sample, comprising the following steps:

(a) contacting a sample comprising at least one CB2 receptor with a compound of formula (I) to determine a baseline signal;
(b) contacting the sample with the dose of said compound suspected to bind to the CB2 receptor and a compound of formula (I);
(c) monitoring the displacement of the compound of formula (I) by the compound suspected to bind to the CB2 receptor; and
(d) calculating the percentage of the CB2 receptors that is occupied by the compound suspected to bind to the CB2 receptor.

The invention also relates to a method for measuring in a living vertebrate, including a human subject, the percentage of CB2 receptors occupied by a compound suspected to bind to the CB2 receptor when a dose of said compound is administered to the vertebrate comprising the following steps:

(a) administering to the vertebrate a compound of formula (I) to determine a baseline signal;
(b) co-administering to the vertebrate the dose of said compound suspected to bind to the CB2 receptor and a compound of formula (I);
(c) monitoring the displacement of the compound of formula (I) by the compound suspected to bind to the CB2 receptor; and
(d) calculating the percentage of the CB2 receptors that is occupied by the compound suspected to bind to the CB2 receptor.

The invention also relates to a method for determining the dose of a CB2 ligand that needs to be administered to a vertebrate, including a human subject, in need thereof comprising the following steps:

(a) administering to the vertebrate a compound of formula (I) and determining the baseline signal;
(b) administering to the vertebrate different doses of CB2 ligand and concomitantly administering to the vertebrate a compound of formula (I);
(c) monitoring the displacement of the compound of formula (I) by the different doses of CB2 ligand; and
(d) calculating the percentage of CB2 receptors that is occupied by the CB2 ligand and determining the dose/occupancy relationship.

In steps (a) above, the baseline signal is considered as 100%.

The invention also relates to a method for determining whether a disease is characterized by a change in the expression of the CB2 receptor comprising the following steps:

(a) contacting a sample or administering to a subject affected with said disease and a healthy sample or a healthy subject with a compound of formula (I);
(b) monitoring in both samples whether the binding of the compound of formula (I) has occurred; and
(c) comparing in both samples the amount of compound of formula (I) that is bound to the CB2 receptors.

Imaging techniques for performing the steps mentioned above include, but are not limited to, positron emission tomography (PET) or single-photon emission computed tomography (SPECT), in particular PET.

The invention also relates to a method of the invention wherein autoradiography is used during the monitoring.

The invention further relates to a pharmaceutical composition comprising a compound of formula (I).

The invention also relates to a compound of formula (I) for use as a diagnostic agent, i.e. for use in the diagnostic of a disease.

The invention also relates to a compound of formula (I) for use in the diagnostic of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

BRIEF DESCRIPTION OF THE DRAWINGS

FIG. 1 depicts time activity curves in the rat spleen and muscle after iv administration of [$^{18}$F]3-fluoropropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate (Example 1, Non-deuterated) and [$^{18}$F](1,1,2,2,3,3-hexadeuterio-3-fluoro-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate (Example 2, Deuterated). Displacement in the chasing experiments was done by administration of GW405833 (CAS 180002-83-9) (iv, 1.5 mg/kg) 10 min after tracer injection.

The synthesis of the compound of formula (I) can, for example, be accomplished according to the following scheme.

Scheme 1

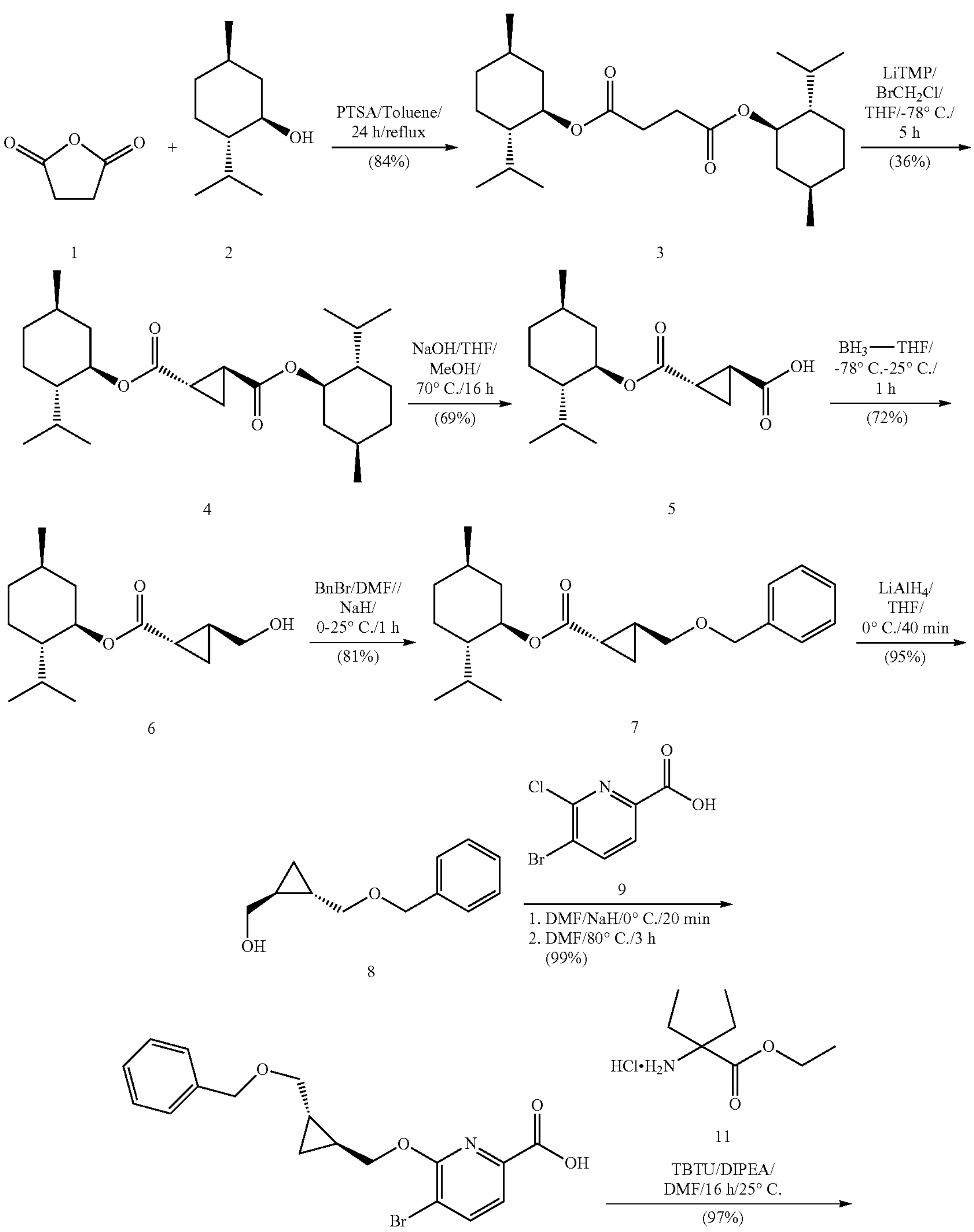

1 2 3

4 5

6 7

9

8

11

10

-continued

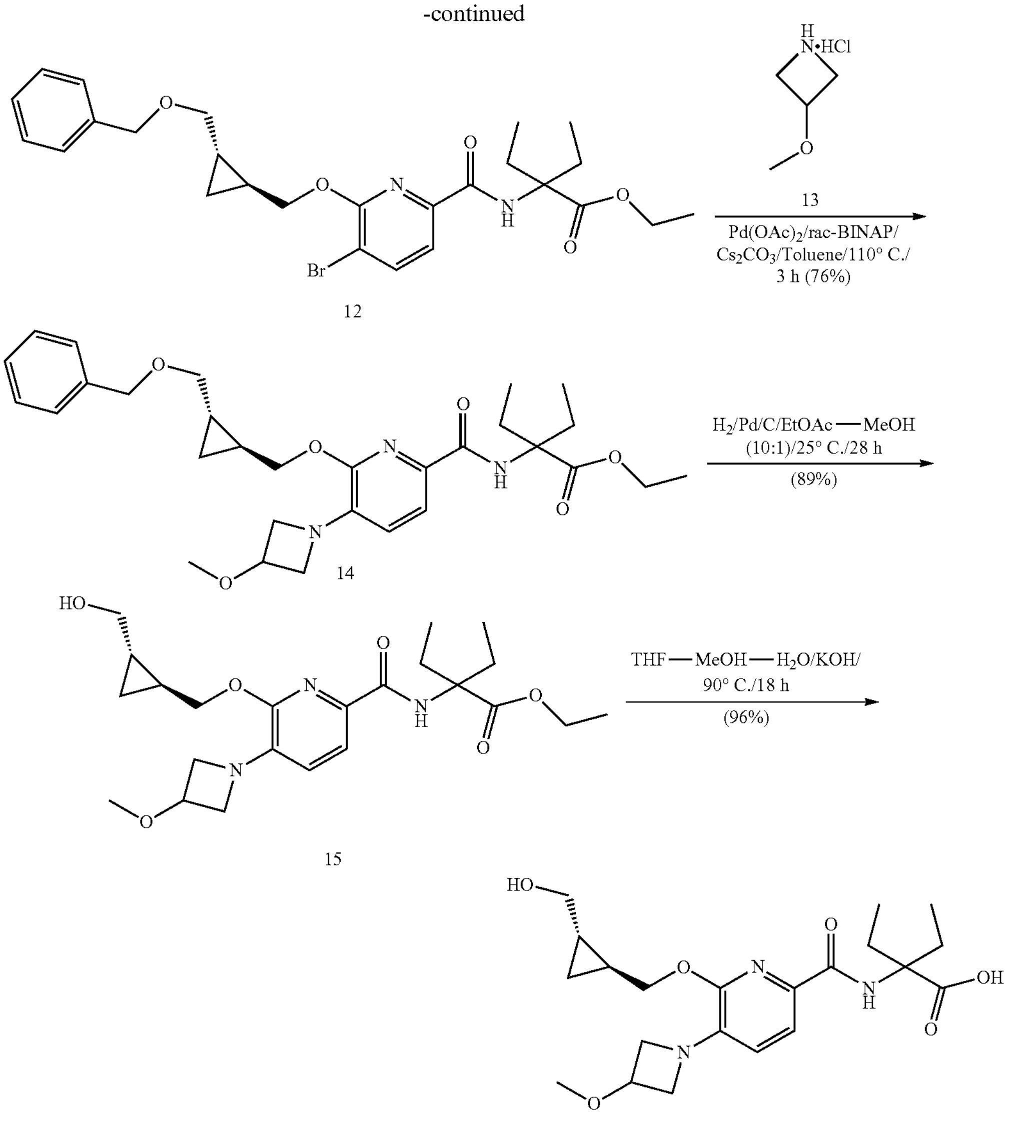

12

14

15

16

Carboxylic acid precursor 16 for target compounds 3-[$^{18}$F]fluoranylpropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate (Ia) and (1,1,2,2,3,3-hexadeuterio-3-[$^{18}$F]fluoranyl-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate (Ib) can be generated from commercially available succinic anhydride 1, 1-menthol 2 and 5-bromo-6-chloropyridine-2-carboxylic acid 9 as described in scheme 1 or by applying another synthetic strategy known to a person skilled in the art.

Scheme 2

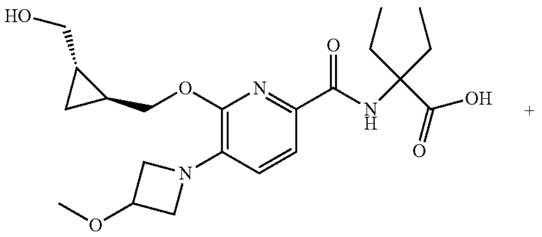

16

-continued

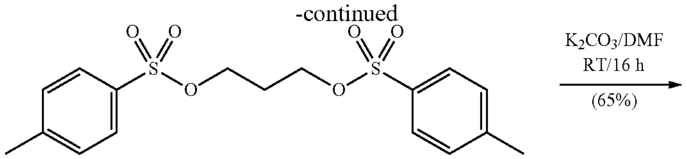

17

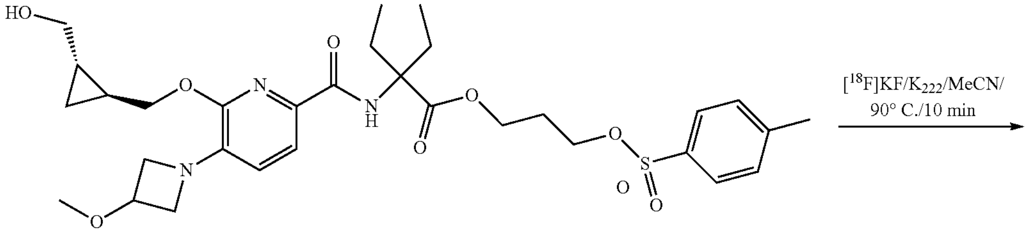

18

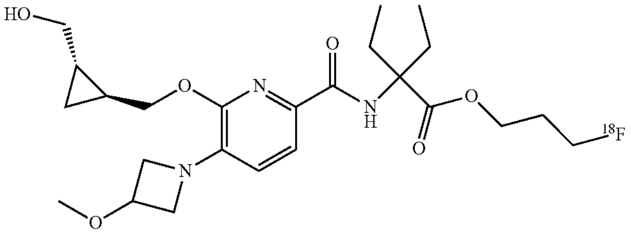

Ia

The target compound (Ia) is accessible via a two-step procedure starting from carboxylic acid 16 and bis-tosylate 17 as described in scheme 2. In the second step $^{18}$F can be introduced in high specific activity via no-carrier-added nucleophilic substitution using [$^{18}$F]KF/Kryptofix 2.2.2 in acetonitrile or any other method known to a person skilled in the art.

Scheme 3

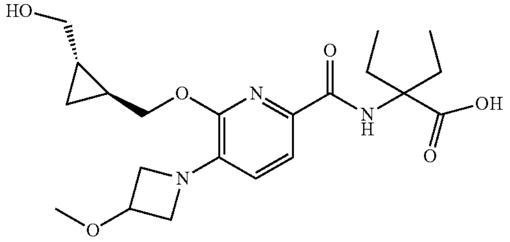

16

+

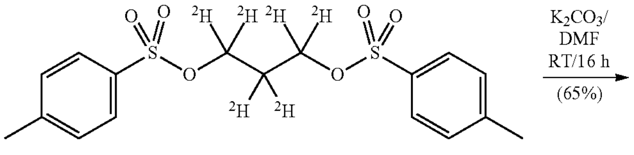

19

-continued

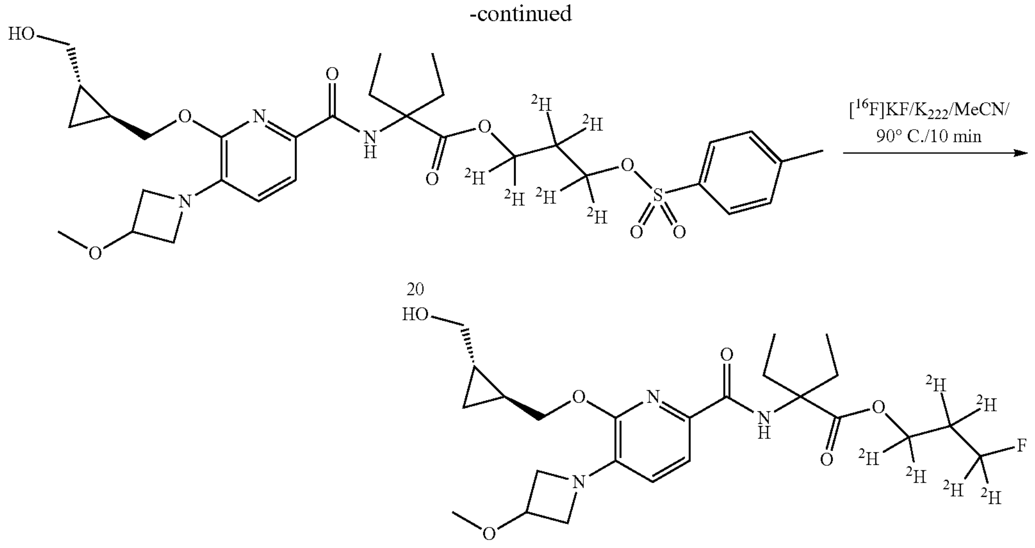

20

Ib

Deuterated target compound (Ib) is accessible in analogy to its non deuterated analogue (Ia) via a two-step procedure starting from carboxylic acid 16 and hexadeutero bis-tosylate 19 as described in scheme 3. In the second step $^{18}$F can be introduced in high specific activity via no-carrier-added nucleophilic substitution using [$^{18}$F]KF/Kryptofix 2.2.2 in acetonitrile or any other method known to a person skilled in the art.

Scheme 4

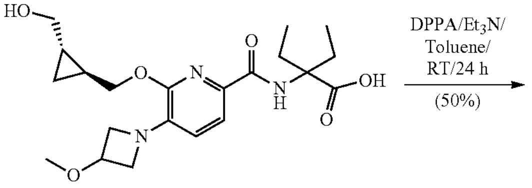

16

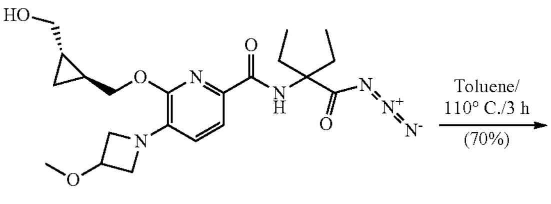

21

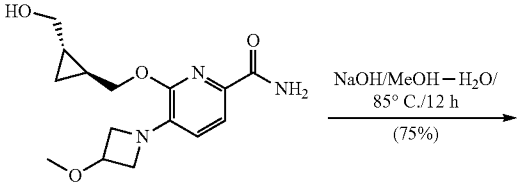

22

-continued

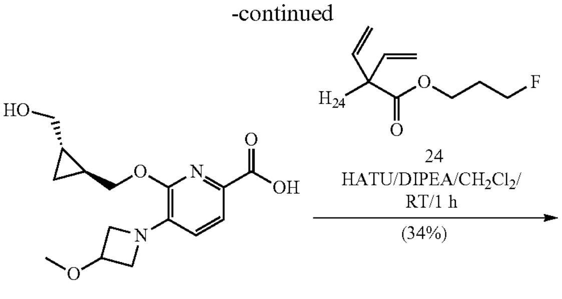

23

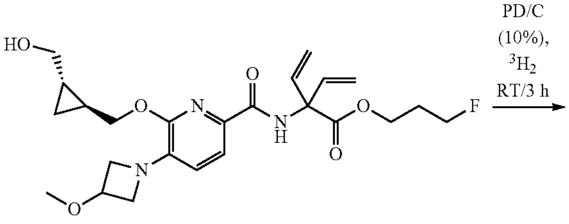

25

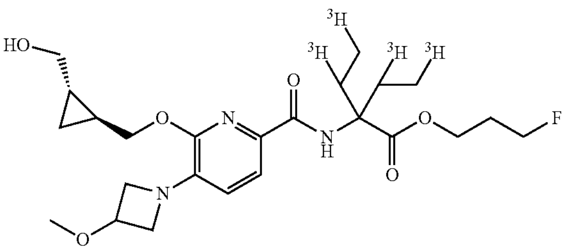

Ic

Tritiated target compound (Ic) can be synthesized from carboxylic acid 16 and amine 24 following the procedure described in scheme 4 or any other route know to a person skilled in the art. In the radiolabeling step bis-olefin 25 is subjected to a reduction with tritium gas to provide 3-fluoropropyl 2-(1,2-ditritioethyl)-2-[[6-[[(1S,2S)-2-(hydroxymethyl)cyclopropyl]methoxy]-5-(3-methoxyazetidin-1-yl)pyridine-2-carbonyl]amino]-3,4-ditritio-butanoate.

The invention thus also relates to a process for the manufacture of a compound of formula (I) comprising on of the following steps:

(a) reacting a compound of formula (A)

(A)

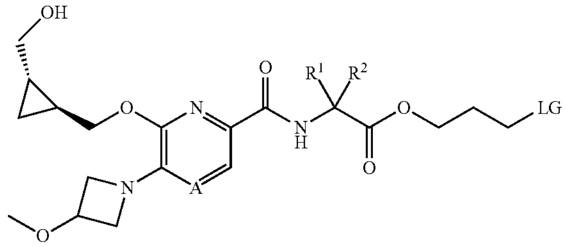

with a nucleophilic [$^{18}$F]fluoride reagent; or (b) reacting a compound of formula (B)

(B)

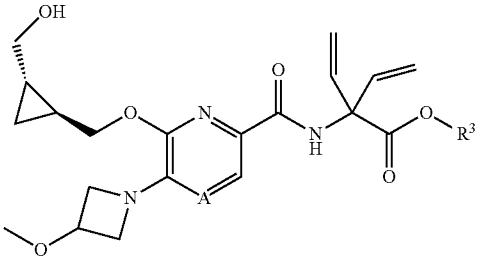

with [$^3$H]$_2$;

wherein LG is a leaving group and wherein $R^1$ to $R^3$ are as defined above.

The leaving group is for example p-tolylsulfonyloxy, 4-nitrobenzenesulfonyloxy, methanesulfonyloxy or trifluoromethanesulfonyloxy.

In step (a), the [$^{18}$F]fluoride reagent can for example be [$^{18}$F]KF/$K_{2.2.2}$.

Step (a) can be for example performed in acetonitrile.

Step (a) can be performed at a temperature of between 25 and 200° C. but heating is not necessary.

The invention further relates to a compound manufactured according to a process of the invention.

The invention will now be illustrated by the following examples which have no limiting character.

EXAMPLES

Abbreviations rac-BINAP=racemic 2,2'-bis(diphenylphosphino)-1,1'-binaphthyl); CAN=chemical abstracts service number; DCM=dichloromethane; DIPEA=N-ethyl-N-isopropylpropan-2-amine; DMF=dimethylformamide; DPPA=diphenylphosphoryl azide; EI=electron impact; EtOAc=ethyl acetate; HATU=1-[bis(dimethylamino)methylene]-1H-1,2,3-triazolo[4,5-b]pyridinium 3-oxid hexafluorophosphate; LAH=Lithiumaluminiumhydrid; LC=liquid chromatography; LiTMP=lithium 2,2,6,6-tetramethylpiperidine; MS=mass spectrometry; NMR=nuclear magnetic resonance; NMR data are reported in parts per million (δ) relative to internal tetramethylsilane and are referenced to the deuterium lock signal from the sample solvent ($d_6$-

DMSO unless otherwise stated); coupling constants (J) are in Hertz; PTSA=p-toluenesulfonic acid; Rt=retention time; SOR=specific optical rotation; TBTU=O-(benzotriazol-1-yl)-N,N,N',N'-tetramethyl-uronium-tetrafluoroborate; THF=tetrahydrofuran.

Experimental

All reactions were undertaken in flame dried glassware. Analytical grade solvents were used for reactions and when required, dry solvents were used without further purification. Reagents were purchased from reputable commercial suppliers and used without further purification, unless otherwise stated. All $^1$H NMR spectra were recorded on a Bruker Advance Ultra Shield 300 MHz spectrometer. Chemical shifts are reported relevant to the stated deuterated solvent. Mass spectra were recorded on PE Sciex API 150EX LC/MS Turbo Spray System. Flash chromatography was conducted using an Isco Combi Flash companion, using prepacked silica columns (230-400 mesh, 40-63 μm) of various sizes from various commercial suppliers. Thin layer chromatography was carried on pre-coated plates (20×20 cm, silica gel F254) purchased from Merck KgaA and was visualized using a 254 nm CAMAG UV lamp or using a basic potassium permanganate solution. All reactions were monitored using a combination of thin layer chromatography, LCMS and $^1$H NMR.

Example 1

3-[$^{18}$F]Fluoropropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

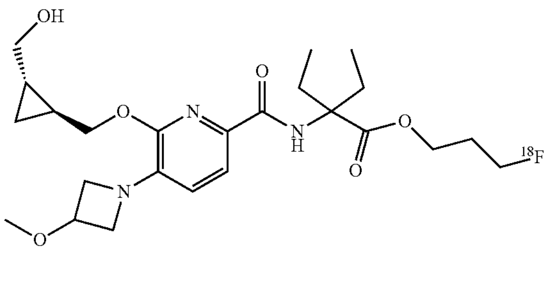 [SMILES: CCC(CC)(NC(=O)c1ccc(N2CC(OC)C2)c(OC[C@H]2C[C@@H]2CO)n1)C(=O)OCCC[18F]]

a) Bis(1R,2S,5R)-5-methyl-2-(propan-2-yl)cyclohexyl Butanedioate

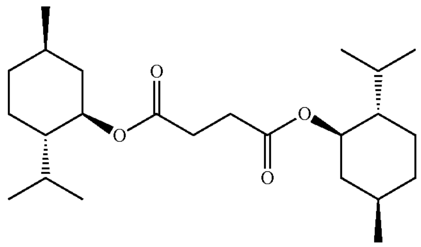 [SMILES: CC(C)[C@@H]1CC[C@@H](C)C[C@H]1OC(=O)CCC(=O)O[C@@H]1C[C@H](C)CC[C@H]1C(C)C]

A 2 L one-necked, round bottom flask was equipped with a stirrer, a Dean-Stark trap and a condenser. The flask was charged with succinic anhydride (64 g, 0.64 mol, 1 eq.), 1-menthol (200 g, 1.3 mol, 2 eq.), p-toluenesulfonic acid monohydrate (1.1 g, 6.39 mmol, 0.01 eq.) and toluene (576 mL). The mixture was heated under reflux for 24 h, cooled to 25° C., diluted with hexane (640 mL) and poured into a mixture of aqueous saturated sodium bicarbonate (800 mL), methanol (320 mL) and water (320 mL). The layers were separated and the aqueous phase was extracted with hexane (2×320 mL). The organic phases were combined, washed with brine (640 mL), dried over sodium sulphate and filtered. The solvent was removed under reduced pressure and the crude product was dissolved in methanol (240 mL). The solution was cooled to +4° C. for 16 h to form colorless crystals which were collected by filtration with suction. The crystals were purified by recrystallization from methanol (240 mL) to afford pure bis(1R,2S,5R)-5-methyl-2-(propan-2-yl)cyclohexyl butanedioate (212 g, 84%).

SOR value: [−87.64°] at t≅25° C., 1.0132% solution in $CHCl_3$.

b) 1,2-Bis(1R,2S,5R)-5-methyl-2-(propan-2-yl)cyclohexyl (1S,2S)-cyclopropane-1,2-dicarboxylate

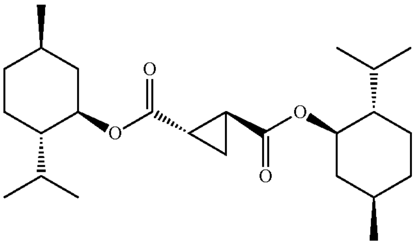 [SMILES: CC(C)[C@@H]1CC[C@@H](C)C[C@H]1OC(=O)[C@H]1C[C@@H]1C(=O)O[C@@H]1C[C@H](C)CC[C@H]1C(C)C]

A 1.8 M solution of butyllithium in THF (152.2 mmol, 84 mL) was added to 225 mL of THF at 0° C. under a $N_2$ atmosphere. Under stirring lithium tetramethylpiperidide (28.2 mL, 167 mmol) was added drop wise over a 20 min period. Stirring was continued at 0° C. for 1 h. Then the reaction mixture was cooled to −78° C. A solution of bis(1R,2S,5R)-5-methyl-2-(propan-2-yl)cyclohexyl butanedioate (30 g, 76.1 mmol) in THF (60 mL) was added drop wise over a 20 min period. The yellow solution was stirred for 1 h. Bromochloromethane (4.08 mL, 60.91 mmol) was added drop wise over a 20 min period. The mixture was stirred for 3 h at −78° C. A saturated aqueous solution of $NH_4Cl$ (120 mL) was added. After stirring for 30 min at 25° C. the mixture was extracted with EtOAc (3×150 mL). The combined organic layers were washed with brine (200 mL), dried over $Na_2SO_4$, filtered, and concentrated in vacuo. The crude was purified by column chromatography ($SiO_2$, 100-200 mesh, 0.5-1% of ethyl acetate and hexane) to afford the title compound (38 g, 42%) as colorless crystals. Recrystallization of this material from methanol (380 mL) provided pure 1,2-bis(1R,2S,5R)-5-methyl-2-(propan-2-yl)cyclohexyl (1S,2S)-cyclopropane-1,2-dicarboxylate (27 g, 36%).

SOR value: [+18.18°] at t≅25° C., 1.0288% solution in $CHCl_3$.

c) (1S,2S)-Cyclopropane-1,2-dicarboxylic acid mono-((1R,2S,5R)-2-isopropyl-5-methyl-cyclohexyl) ester

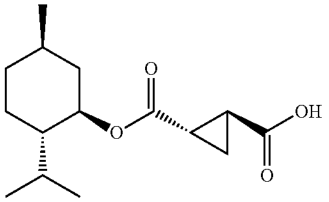 [SMILES: CC(C)[C@@H]1CC[C@@H](C)C[C@H]1OC(=O)[C@H]1C[C@@H]1C(=O)O]

To a solution of 1,2-bis(1R,2S,5R)-5-methyl-2-(propan-2-yl)cyclohexyl (1S,2S)-cyclopropane-1,2-dicarboxylate (25 g, 61.58 mmol) in isopropanol (250 mL) was added a 5 M solution of NaOH (13.54 mL, 67.73 mmol) at 25° C. The mixture was stirred at 70° C. for 16 h. The organic solvent was removed under reduced pressure. Water (200 mL) was added and the mixture was washed with diethyl ether (2×150 mL). The aqueous layer was acidified with 2 N HCl (pH ~2) and extracted with ethyl acetate (3×250 mL). The combined organic layers were dried over $Na_2SO_4$, filtered and concentrated under reduced pressure to get (1S,2S)-2-({[(1R,2S,5R)-5-methyl-2-(propan-2-yl) cyclohexyl]oxy}carbonyl) cyclopropane-1-carboxylic acid (11.4 g, 69%) as off white semisolid.

d) (1R,2S,5R)-5-Methyl-2-(propan-2-yl)cyclohexyl (1S,2S)-2-(hydroxymethyl) cyclopropane-1-carboxylate

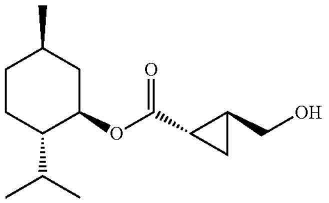 [SMILES: CC(C)[C@@H]1CC[C@@H](C)C[C@H]1OC(=O)[C@H]1C[C@@H]1CO]

To a stirred solution of (1S,2S)-cyclopropane-1,2-dicarboxylic acid mono-((1R,2S,5R)-2-isopropyl-5-methyl-cyclohexyl) ester (20 g, 74.63 mmol) in THF (200 mL) was added a 1 M solution of borane in THF (56 mL) drop wise at −78° C. The mixture was stirred for 1 h at 25° C. and quenched with aq. $NH_4Cl$ solution (150 mL). The organic solvent was removed under reduced pressure. Water was added (50 mL) and the mixture was extracted with ethyl acetate (2×100 mL). The combined organic layers were washed with brine (80 mL), dried over $Na_2SO_4$, filtered and concentrated under reduced pressure. The crude was purified by silica gel column chromatography (15-19% ethyl acetate/hexane) to get (1R,2S,5R)-5-methyl-2-(propan-2-yl) cyclohexyl (1S,2S)-2-(hydroxymethyl) cyclopropane-1-carboxylate (13.7 g, 72%) as yellowish semi solid.

e) (1R,2S,5R)-5-Methyl-2-(propan-2-yl)cyclohexyl (1S,2S)-2-[(benzyloxy) methyl] cyclopropane-1-carboxylate

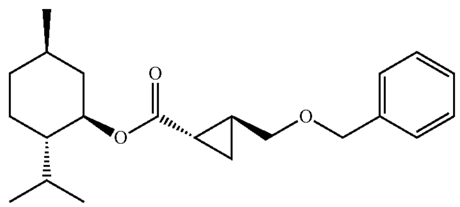 [SMILES: CC(C)[C@@H]1CC[C@@H](C)C[C@H]1OC(=O)[C@H]1C[C@@H]1COCc1ccccc1]

To a stirred solution of (1R,2S,5R)-5-methyl-2-(propan-2-yl)cyclohexyl (1S,2S)-2-(hydroxymethyl) cyclopropane-1-carboxylate (20 g, 78.74 mmol) in DMF (140 mL) was added NaH (4.72 g, 118.11 mmol) at 0° C. The mixture was stirred at 25° C. for 30 min. Benzylbromide (18.7 mL, 157.5 mmol) was added and stirring was continued at 25° C. for 30 min. Aqueous $NH_4Cl$ solution (150 mL) was added and the mixture was extracted with EtOAc (2×150 mL). The combined organic layers were washed with water (3×120 mL), dried over $Na_2SO_4$, filtered and concentrated under reduced pressure. The crude was purified by silica gel column chromatography (1.9% EtOAc/hexane) to get (1R,2S,5R)-5-methyl-2-(propan-2-yl)cyclohexyl (1S,2S)-2-[(benzyloxy)methyl]cyclopropane-1-carboxylate (22 g, 8%) as light yellow oil.

f) [(1S,2S)-2-[(Benzyloxy)methyl]cyclopropyl] methanol

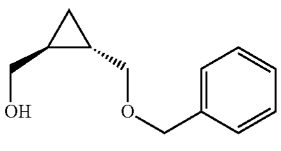 [SMILES: OC[C@H]1C[C@@H]1COCc1ccccc1]

To a stirred solution of (1R,2S,5R)-5-methyl-2-(propan-2-yl)cyclohexyl (1S,2S)-2-[(benzyloxy) methyl] cyclopropane-1-carboxylate (10 g, 29.01 mmol) in THF (200 mL) was added LAH (58.1 mL, 1 M in THF) at 0° C. The reaction mixture was stirred for 40 min at 0° C. and quenched with aq $NH_4Cl$ solution (100 mL). The organic solvent was removed under reduced pressure. The solution was extracted with ethyl acetate (3×100 mL). The combined organic layers were brought to dryness and the crude was purified using silica gel column chromatography (30-35% ethyl acetate/hexane) to get [(1S,2S)-2-[(benzyloxy)methyl] cyclopropyl] methanol (5.33 g, 95%) as light yellow oil.

g) 6-{[(1S,2S)-2-[(Benzyloxy)methyl]cyclopropyl] methoxy}-5-bromopyridine-2-carboxylic Acid

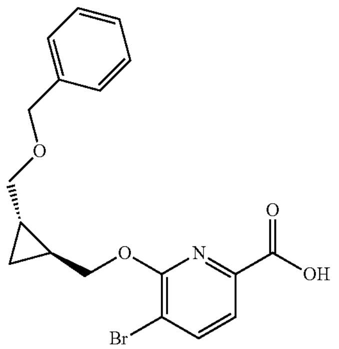 [SMILES: O=C(O)c1ccc(Br)c(OC[C@H]2C[C@@H]2COCc2ccccc2)n1]

To a solution of 5-bromo-6-chloropyridine-2-carboxylic acid (CAN 959958-25-9, 4 g, 19.80 mmol) in DMF (45 mL) was added NaH (2.77 g, 69.31 mmol) portion wise at 0° C. and stirred for 20 min at 0° C. [(1S,2S)-2-[(benzyloxy) methyl]cyclopropyl]methanol (4.18 g, 21.78 mmol) in DMF (15 mL) was added drop wise at 0° C. The mixture was stirred for 15 min at 25° C., heated to 80° C. for 3 h, cooled to 25° C. and quenched with 2 N aq. HCl to pH ~2. Water (100 mL) was added and the mixture was extracted with EtOAc (3×150 mL). The combined organic layers were washed with water (4×50 mL) and brine (50 mL), dried over $Na_2SO_4$ and concentrated under reduced pressure to get 6-{[(1S,2S)-2-[(benzyloxy)methyl] cyclopropyl]methoxy}-5-bromopyridine-2-carboxylic acid (7.7 g, 99%) as off white sticky liquid.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 76.8%, Rt=2.60 min, MS calculate: 391, MS found: 391.8 ($[M+H]^+$).

h) Ethyl 2-[(6-{[(1S,2S)-2-[(benzyloxy)methyl]cyclopropyl]methoxy}-5-bromopyridin-2-yl)formamido]-2-ethylbutanoate

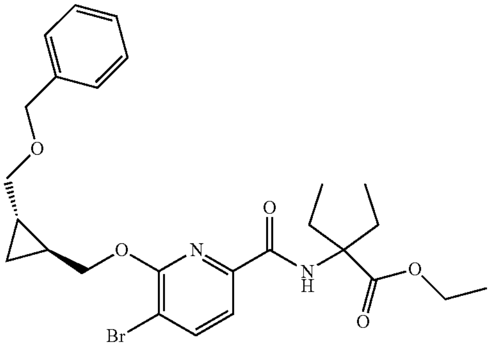 [SMILES: CCOC(=O)C(CC)(CC)NC(=O)c1ccc(Br)c(OC[C@H]2C[C@@H]2COCc2ccccc2)n1]

To a solution of 6-{[(1S,2S)-2-[(benzyloxy)methyl]cyclopropyl]methoxy}-5-bromopyridine-2-carboxylic acid (15.5 g, 39.54 mmol) in DMF (100 mL) were added DIPEA (27.49 mL, 158.16 mmol), ethyl 2-amino-2-ethylbutanoate (CAN 189631-96-7, 7.73 g, 39.54 mmol) and TBTU (15.25 g, 47.449 mmol). The reaction mixture was stirred at 25° C. for 16 h, poured into water (170 mL) and extracted with EtOAc (3×200 mL). The combined organic layers were washed with water (4×120 mL) and brine (100 mL), dried over $Na_2SO_4$, filtered and brought to dryness. The crude was purified via silica gel column chromatography (25% ethyl acetate/hexanes) to get ethyl 2-[(6-{[(1S,2S)-2-[(benzyloxy) methyl]cyclopropyl]methoxy}-5-bromopyridin-2-yl)formamido]-2-ethylbutanoate (20.5 g, 97%) as light brown oil.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 91.47%, Rt=2.58 min, MS calculate: 533, MS found: 533.0 [$(M+H]^+$).

i) Ethyl 2-[(6-{[(1S,2S)-2-[(benzyloxy) methyl] cyclopropyl] methoxy}-5-(3-methoxyazetidin-1-yl) pyridin-2-yl)formamido]-2-ethylbutanoate

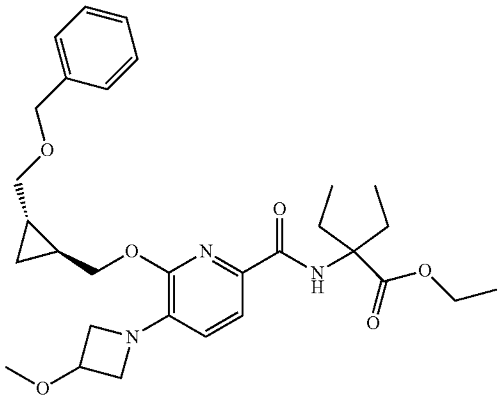 [SMILES: CCOC(=O)C(CC)(CC)NC(=O)c1ccc(N2CC(OC)C2)c(OC[C@H]2C[C@@H]2COCc2ccccc2)n1]

To a solution ethyl 2-[(6-{[(1S,2S)-2-[(benzyloxy) methyl]cyclopropyl]methoxy}-5-bromopyridin-2-yl)formamido]-2-ethylbutanoate (4.0 g, 7.5 mmol) in toluene (160 mL) were added 3-methoxyazetidine (1.39 g, 11.3 mmol) and cesium carbonate (7.33 g, 22.5 mmol). The mixture was degassed with argon for 10 min. Rac-BINAP (0.935 g, 1.50 mmol) and Pd(II)acetate (0.34 g, 1.50 mmol) were added. The mixture was heated to 110° C. for 3 h, diluted with EtOAc (100 mL), filtered through a celite bed and washed with EtOAc (3×100 mL). The filtrate was concentrated and the crude purified through silica gel column chromatography (42-50% ethyl acetate/hexanes) to get ethyl 2-[(6-{[(1S,2S)-2-[(benzyloxy)methyl]cyclopropyl]methoxy}-5-(3-methoxyazetidin-1-yl)pyridin-2-yl)formamido]-2-ethylbutanoate (3.1 g, 76%) as light brown oil.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 96.7%, Rt=2.37 min, MS calculate: 539, MS found: 539.9 ($[M+H]^+$).

j) Ethyl 2-ethyl-2-[(6-{[(1S,2S)-2-(hydroxymethyl) cyclopropyl]methoxy}-5-(3-methoxyazetidin-1-yl) pyridin-2-yl)formamido]butanoate

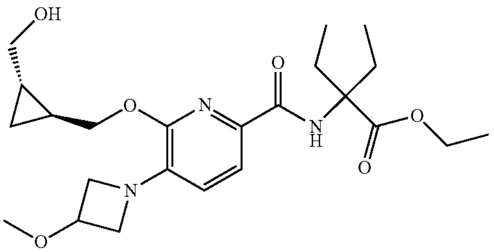 [SMILES: CCOC(=O)C(CC)(CC)NC(=O)c1ccc(N2CC(OC)C2)c(OC[C@H]2C[C@@H]2CO)n1]

A stirred solution of ethyl 2-[(6-{[(1S,2S)-2-[(benzyloxy) methyl]cyclopropyl] methoxy}-5-(3-methoxyazetidin-1-yl) pyridin-2-yl)formamido]-2-ethylbutanoate (26 g, 48.24 mmol) in 735 mL EtOAc:MeOH (10:1) was degassed for 30 min. Pd/C (10%) (6.5 g) was added. The mixture was hydrogenated under a hydrogen atmosphere at 40 PSI for 28 h at 25° C., filtered through a celite bed and washed with 10% MeOH/EtOAc (4×200 mL). The filtrate was evaporated under reduced pressure to get the crude. The crude was purified applying silica gel column chromatography (10-50% EtOAc:hexanes) to get ethyl 2-ethyl-2-[(6-{[(1S,2S)-2-(hydroxymethyl)cyclopropyl]methoxy}-5-(3-methoxyazetidin-1-yl)pyridin-2-yl)formamido] butanoate (19.3 g, 89%) as colorless sticky liquid.

SOR value: [+15.51°] at t≅20° C., 0.2514% in MeOH.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 98.9%, Rt=3.26 min, MS calculate: 449, MS found: 449.9 ($[M+H]^+$).

k) 2-Ethyl-2-[(6-{[(1S,2S)-2-(hydroxymethyl)cyclopropyl]methoxy}-5-(3-methoxyazetidin-1-yl)pyridin-2-yl)formamido]butanoic Acid

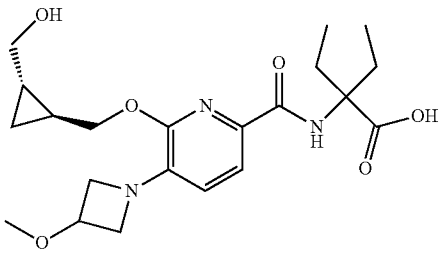 [SMILES: CCC(CC)(NC(=O)c1ccc(N2CC(OC)C2)c(OC[C@H]2C[C@@H]2CO)n1)C(=O)O]

In a 25 ml round-bottomed flask, ethyl 2-ethyl-2-[(6-{[(1S,2S)-2-(hydroxymethyl) cyclopropyl]methoxy}-5-(3-methoxyazetidin-1-yl)pyridin-2-yl)formamido]butanoate (100 mg, 0.22 mmol) was combined with THF (2.0 mL), MeOH (2.2 mL) and water (2.0 mL) to give a light yellow solution. KOH pellets (62 mg, 1.11 mmol) were added. The mixture was heated to 90° C. After 18 h the organic solvent was removed under reduced pressure. The aqueous phase was diluted with water (20 mL) and extracted with diethyl ether (2×10 mL). The combined organic layers were discarded. The aqueous phase was adjusted to pH~2 (1 M HCl) and extracted with EtOAc (3×15 mL). The combined organic layers were washed with brine (10 mL), dried, filtered and brought to dryness under reduced pressure to get pure 2-ethyl-2-[(6-{[(1S,2S)-2-(hydroxymethyl)cyclopropyl]methoxy}-5-(3-methoxyazetidin-1-yl)pyridin-2-yl)formamido]butanoic acid (90 mg, 96%) as colorless sticky mass.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 95.5%, Rt=2.00 min, MS calculate: 419, MS found: 420.4 ($[M+H]^+$).

l) 3-{[(4-Methylbenzene)sulfonyl]oxy}propyl 2-ethyl-2-[(6-{[(1S,2S)-2-(hydroxymethyl)cyclopropyl]methoxy}-5-(3-methoxyazetidin-1-yl)pyridin-2-yl)formamido]butanoate

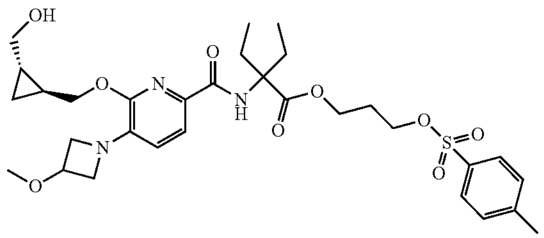

To a solution of 2-ethyl-2-[(6-{[(1S,2S)-2-(hydroxymethyl)cyclopropyl]methoxy}-5-(3-methoxyazetidin-1-yl) pyridin-2-yl)formamido]butanoic acid (260 mg, 0.62 mmol) in DMF (5 mL) were added $K_2CO_3$ (256 mg, 1.85 mmol) and 3-{[(4-methylbenzene)sulfonyl]oxy}propyl 4-methylbenzene-1-sulfonate (711 mg, 1.85 mmol). The reaction mixture was stirred for 16 h at 25° C., poured into water, quenched with aq. 1 (N) HCl and extracted with EtOAc (3×40 mL). The combined organic layers were washed with brine (30 mL), dried, filtered and concentrated in vacuo to get crude product which was purified by combiflash using silica column and 20-80% EtOAc in hexane to get pure 3-{[(4-methylbenzene) sulfonyl]oxy}propyl 2-ethyl-2-[(6-{[(1S,2S)-2-(hydroxymethyl)cyclopropyl]methoxy}-5-(3-methoxyazetidin-1-yl)pyridin-2-yl)formamido]butanoate (255 mg, 65%) as colorless sticky mass.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 90.7%, Rt=3.48 min, MS calculate: 633, MS found: 634.4 ($[M+H]^+$).

m) 3-[$^{18}$F]Fluoropropyl 2-ethyl-2-[[6-[[(1S,2S)-2-(hydroxymethyl)cyclopropyl]methoxy]-5-(3-methoxyazetidin-1-yl)pyridine-2-carbonyl]amino] butanoate

[$^{18}$F]Fluoride ions were obtained from bombardment of 98% enriched $^{18}$O-water via the e $^{18}O(p,n)^{18}F$ nuclear reaction in a Cyclone 18/9 cyclotron (18-MeV; IBA Belgium), trapped on an anion exchange cartridge (Waters SepPak Accell QMA cartridge carbonate) and subsequently eluted with a solution of $K_2CO_3$ (1 mg/mL) and $Krypofix_{222}$ (2.5 mg/mL) in water/MeCN 1:3. Volatiles were removed at 110° C. under reduced pressure and with a gentle flow of nitrogen. Azeotropic drying was carried out using MeCN (3×1 mL). Upon addition of 3-{[(4-methylbenzene)sulfonyl]oxy}propyl 2-ethyl-2-[(6-{[(1S,2S)-2-(hydroxymethyl)cyclopropyl]methoxy}-5-(3-methoxyazetidin-1-yl)pyridin-2-yl)formamido]butanoate (1 mg in 0.5 mL MeCN), the reaction mixture was stirred at 90° C. for 10 minutes. The reaction mixture was subsequently diluted with water (2.5 mL) and the crude was purified by semi-preparative HPLC (Merck-Hitachi L2130 system), equipped with a radiation detector VRM 202 (Comecer, Netherlands) in combination with an ACE 5 C-18-300 (250×10.0 mm. 5 μm) column and a gradient solvent system: 0.1% H3PO4 in H2O (solvent A), MeCN (solvent B); 0.0-8.0 min, 20% B; 8.1-30.0 min, 20-90% B; 30.1-35.0 min, 90% B; 35.1-37.0 min, 90-20% B; 37.1-43.0 min, 20% B. A flow rate of was 4 mL/min was used and the UV signal detection was conducted at 230 nm. Product fraction of the semipreparative HPLC was collected in 35 mL of water and passed through a C18 cartridge (Waters, pre-conditioned with 5 mL EtOH and 5 mL water). The cartridge was washed with water (5 mL) and the title compound subsequently eluted using 0.5 mL EtOH. The radioligand 3-(18F)fluoranylpropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate was formulated with 5% EtOH in water for injection (WFI). 3-(18F)Fluoranylpropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate was obtained with molar activities ranging from 52-65 GBq/μmol and excellent radiochemical purity (>99%). The decay-corrected radiochemical yield was 9.0±0.4%. Analytical quality control was performed to determine radiochemical and chemical purity, specific activity, and chemical identity on an Agilent 1100 series HPLC system, equipped with UV detector and a GabiStar radiodetector (Raytest). A reverse phase ACE C18-AR column (50×4.6 mm, 3 mm) was used in combination with the following separation conditions: 0.1% TFA in H2O (solvent A), MeCN (solvent B); 0.0-2.0 min, 20% B; 2.1-12.0 min, 20-90% B; 12.1-14.0 min, 90% B; 14.1-15.0 min, 90-20% B; 15.1-20.0 min, 20% B. The flow rate of 1 mL/min was used and the UV signal was recorded at 230 nm. Molar activities were calculated by comparing the UV intensity of the formulated products with calibration curves of the corresponding non-radioactive standards.

Example 2

(1,1,2,2,3,3-Hexadeuterio-3-[18F]fluoranyl-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

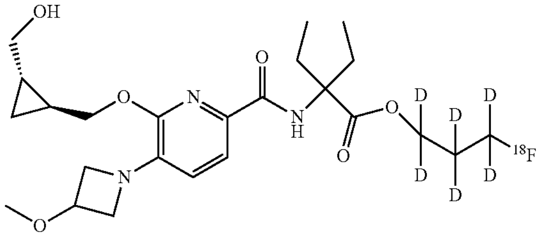 [SMILES: [2H]C([2H])([18F])C([2H])([2H])C([2H])([2H])OC(=O)C(CC)(CC)NC(=O)c1ccc(N2CC(OC)C2)c(OC[C@H]2C[C@@H]2CO)n1]

a) [1,1,2,2,3,3-Hexadeuterio-3-(p-tolylsulfonyloxy) propyl]4-methylbenzenesulfonate

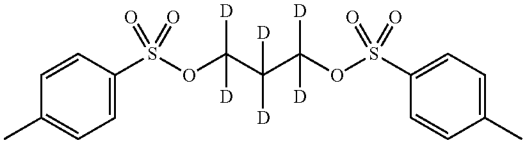

To a solution of 1,1,2,2,3,3-hexadeuteriopropane-1,3-diol (73 mg, 0.87 mmol) in DCM (1 mL) were added 2,6-lutidine (0.5 mL, 4.34 mmol) and tosyl chloride (496 mg, 2.60 mmol, 3 eq.). The reaction mixture was stirred for 17 h at 25° C., diluted with DCM (20 mL), washed with aq. 1 N HCl (10 mL), dried, filtered and concentrated in vacuo. The crude was purified by column chromatography on silica gel (5-30% EtOAc in hexane) to get the title compound (205 mg, 61%) as white solid.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 99.84%, Rt=3.48 min, MS calculate: 390, MS found: 408.1 ($[M+NH_4]^+$).

b) [1,1,2,2,3,3-Hexadeuterio-3-(p-tolylsulfonyloxy) propyl]2-ethyl-2-[[6-[[(1S,2S)-2-(hydroxymethyl) cyclopropyl]methoxy]-5-(3-methoxyazetidin-1-yl) pyridine-2-carbonyl]amino]butanoate

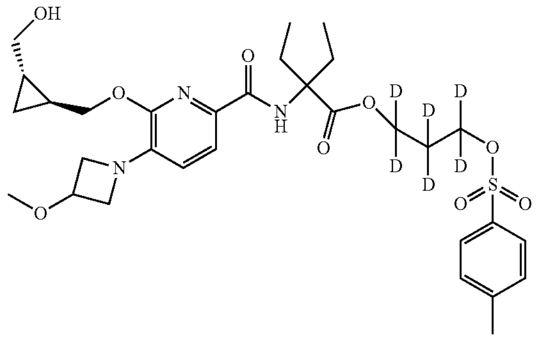 [SMILES: [2H]C([2H])(OC(=O)C(CC)(CC)NC(=O)c1ccc(N2CC(OC)C2)c(OC[C@H]2C[C@@H]2CO)n1)C([2H])([2H])C([2H])([2H])OS(=O)(=O)c1ccc(C)cc1]

To a solution of 2-ethyl-2-[(6-{[(1S,2S)-2-(hydroxymethyl)cyclopropyl]methoxy}-5-(3-methoxyazetidin-1-yl) pyridin-2-yl)formamido]butanoic acid (example 1 k, 50 mg, 0.12 mmol) in DMF (5.0 mL) were added $K_2CO_3$ (49 mg, 0.35 mmol) and [1,1,2,2,3,3-hexadeuterio-3-(p-tolylsulfonyloxy)propyl]4-methylbenzenesulfonate (93 mg, 0.24 mmol). The reaction mixture was stirred for 17 h, quenched with water (30 mL) and extracted with EtOAc (3×20 mL). The combined organic layers were washed with brine (20 mL), dried, filtered and concentrated in vacuo. The crude was purified by column chromatography on silica gel (30-80% EtOAc in hexane) to obtain the title compound (50 mg, 67%) as colorless liquid.

LCMS: Column Zorbax Ext C 18 (50×4.6 mm), 5μ, (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition to 4 min and finally back to initial condition in 5 min). Purity is 95.5%, Rt=3.47 min, MS calculate: 639, MS found: 640.3 ($[M+H]^+$).

c) (1,1,2,2,3,3-Hexadeuterio-3-[18F]fluoranyl-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate

[$^{18}$F]Fluoride ions were obtained from bombardment of 98% enriched $^{18}$O-water via the e $^{18}O(p,n)^{18}F$ nuclear reaction in a Cyclone 18/9 cyclotron (18-MeV; IBA Belgium). [$^{18}$F]Fluoride was trapped on an anion exchange cartridge (Waters SepPak Accell QMA cartridge carbonate) and subsequently eluted with a solution of $K_2CO_3$ (1 mg/mL) and $Krypofix_{222}$ (2.5 mg/mL) in water/MeCN 1:3. Volatiles were removed at 110° C. under reduced pressure and with a gentle flow of nitrogen. Azeotropic drying was carried out using MeCN (3×1 mL). Upon addition of [1,1,2,2,3,3-hexadeuterio-3-(p-tolylsulfonyloxy)propyl]2-ethyl-2-[[6-[[(1S,2S)-2-(hydroxymethyl)cyclopropyl]methoxy]-5-(3-methoxyazetidin-1-yl)pyridine-2-carbonyl]amino] butanoate (1 mg in 0.5 mL MeCN), the reaction mixture was stirred at 90° C. for 10 minutes. The reaction mixture was subsequently diluted with water (2.5 mL) and the crude was purified by semi-preparative HPLC (Merck-Hitachi L2130 system), equipped with a radiation detector VRM 202 (Comecer, Netherlands) in combination with an ACE 5 C-18-300

(250×10.0 mm, 5 μm) column and a gradient solvent system: 0.1% H3PO4 in H2O (solvent A), MeCN (solvent B); 0.0-8.0 min, 20% B; 8.1-30.0 min, 20-90% B; 30.1-35.0 min, 90% B; 35.1-37.0 min, 90-20% B; 37.1-43.0 min, 20% B. A flow rate of was 4 mL/min was used and the UV signal detection was conducted at 230 nm. Product fraction of the semipreparative HPLC was collected in 35 mL of water and passed through a C18 cartridge (Waters, pre-conditioned with 5 mL EtOH and 5 mL water). The cartridge was washed with water (5 mL) and the title compound subsequently eluted using 0.5 mL EtOH. The radioligand (1,1,2,2,3,3-hexadeuterio-3-($^{18}$F)fluoranyl-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate was formulated with 5% EtOH in water for injection (WFI). radioligand (1,1,2,2,3,3-hexadeuterio-3-(18F)fluoranyl-propyl) 2-ethyl-2-[[6-[[(1S,2S)-2-(hydroxymethyl)cyclopropyl]methoxy]-5-(3-methoxyazetidin-1-yl)pyridine-2-carbonyl]amino]butanoate was obtained with molar activities ranging from 27-44 GBq/μmol and excellent radiochemical purity (>99%). The decay-corrected radiochemical yield was 5.0±1.1%. Analytical quality control was performed to determine radiochemical and chemical purity, specific activity, and chemical identity on an Agilent 1100 series HPLC system, equipped with UV detector and a GabiStar radiodetector (Raytest). A reverse phase ACE C18-AR column (50×4.6 mm, 3 mm) was used in combination with the following separation conditions: 0.1% TFA in H2O (solvent A), MeCN (solvent B); 0.0-2.0 min, 20% B; 2.1-12.0 min, 20-90% B; 12.1-14.0 min, 90% B; 14.1-15.0 min, 90-20% B; 15.1-20.0 min, 20% B. The flow rate of 1 mL/min was used and the UV signal was recorded at 230 nm. Molar activities were calculated by comparing the UV intensity of the formulated products with calibration curves of the corresponding non-radioactive standards.

Example 3

3-Fluoropropyl 2-(1,2-ditritioethyl)-2-[[6-[[(1S,2S)-2-(hydroxymethyl)cyclopropyl]methoxy]-5-(3-methoxyazetidin-1-yl)pyridine-2-carbonyl]amino]-3,4-ditritio-butanoate

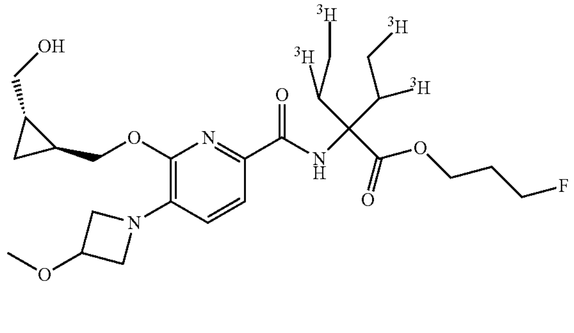 [SMILES: [3H]CC([3H])C(NC(=O)c1ccc(N2CC(OC)C2)c(OC[C@H]2C[C@@H]2CO)n1)(C(=O)OCCCF)C([3H])C[3H]]

a) 2-Ethyl-2-(6-(((1S,2S)-2-(hydroxymethyl)cyclopropyl)methoxy)-5-(3-methoxyazetidin-1-yl)picolinamido)butanoyl Azide

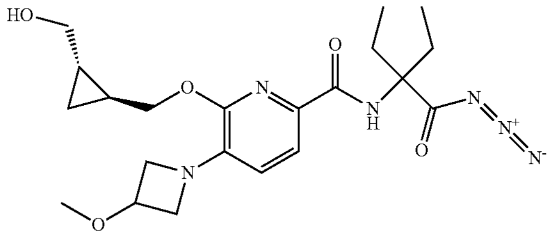 [SMILES: CCC(CC)(NC(=O)c1ccc(N2CC(OC)C2)c(OC[C@H]2C[C@@H]2CO)n1)C(=O)N=[N+]=[N-]]

In a 30 mL round bottom flask 2-ethyl-2-(6-(((1S,2S)-2-(hydroxymethyl) cyclopropyl)methoxy)-5-(3-methoxyazetidin-1-yl)picolinamido)butanoic acid (example 1 k, 338 mg, 802 μmol, 1 eq.) was dissolved in toluene (14 mL). Triethylamine (81 mg, 116 μL, 802 μmol, 1 eq.) and DPPA (221 mg, 173 μL, 802 μmol, 1 eq.) were added. The reaction mixture was stirred for 24 h at ambient temperature, poured onto water (20 mL) and extracted with AcOEt (3×30 mL). The combined organic layers were dried over sodium sulfate and concentrated in vacuo. The crude material was purified by flash chromatography ($SiO_2$, 120 g, 10-70% AcOEt in heptane) to give the title compound (177 mg, 0.396 mmol, 48%) as off-white solid.

$^1$H NMR (600 MHz, $CDCl_3$): δ ppm 8.32 (s, 2H, NH), 7.54-7.59 (d, $^3$J=7.9 Hz, 1H, $N_{Py}$—$C_q$—CH—CH), 6.46-6.53 (d, $^3$J=7.9 Hz, 1H, $N_{Py}$—$C_q$—CH), 4.09-4.30 (m, 8H, m, O—$CH_2$, $CH_2$—N—$CH_2$, $PO_3$—O—$CH_2$, O—CH), 3.72-3.84 (m, 2H, $CH_2$—N—$CH_2$), 3.23 (s, 3H, O—$CH_3$), 2.35-2.51 (m, 2H, $N_3$—CO—$C_q$—$CH_2$), 1.68-1.89 (m, 2H, $N_3$—CO—$C_q$—$CH_2$), 1.24-1.34 (m, 2H, CH—$CH_2$—CH), 0.74 (t, $^3$J=7.5 Hz, 6H, $N_3$—CO—$C_q$—$CH_2$—$CH_3$), 0.63-0.72 (m, 2H, CH—$CH_2$—CH)

HRMS (ESI): $C_{21}H_{30}N_6O_5$ $[M+H]^+$ calculated=447.2304. found=447.2296.

b) 6-(((1S,2S)-2-(Hydroxymethyl)cyclopropyl)methoxy)-5-(3-methoxyazetidin-1-yl)picolinamide

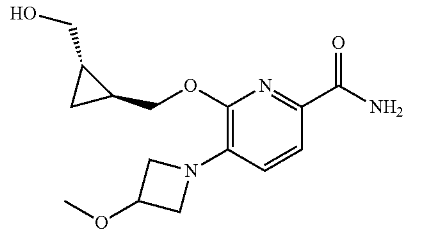 [SMILES: COC1CN(c2ccc(C(N)=O)nc2OC[C@H]2C[C@@H]2CO)C1]

In a 25 mL round bottom flask 2-ethyl-2-(6-(((1S,2S)-2-(hydroxymethyl) cyclopropyl)methoxy)-5-(3-methoxyazetidin-1-yl)picolinamido)butanoyl azide (177 mg, 0.396 mmol, 1 eq.) was dissolved in toluene (10.0 mL). The reaction mixture was heated to 110° C. upon stirring for 3 h and then concentrated in vacuo. THF (3 mL) and 3N NaOH (7 mL) were added. The reaction mixture was heated to 90° C. for 1 h upon stirring, poured onto water (10 mL) and extracted with AcOEt (3×40 mL). The combined organic layers were dried over sodium sulfate and concentrated in vacuo to give the title compound (85 mg, 0.277 mmol, 70%) as light orange oil. The crude material was used in the next step without further purification.

$^{1}H$ NMR (600 MHz, $CDCl_3$): δ ppm 8.18 (CO—$NH_2$), 7.74 (d, $^{3}J$=8.0 Hz, 1H, $N_{Py}$—$C_q$—CH—CH), 6.56 (d, $^{3}J$=8.0 Hz, 1H, $N_{Py}$—$C_q$—CH), 3.99-4.41 (m, 7H, O—$CH_2$, $CH_2$—N—$CH_2$, O—CH, HO—$CH_2$), 3.95-4.00 (m, 2H, $CH_2$—N—$CH_2$), 3.29 (m, 3H, O—$CH_3$), 1.20-1.36 (CH—$CH_2$—CH), 0.54-0.79 (m, 2H, CH—$CH_2$—CH)

MS (ESI): $C_{15}H_{21}N_3O_4$ $[M+H]^+$ calculated=308.14. found=308.20.

c) 6-(((1S,2S)-2-(Hydroxymethyl)cyclopropyl) methoxy)-5-(3-methoxyazetidin-1-yl)picolinic Acid

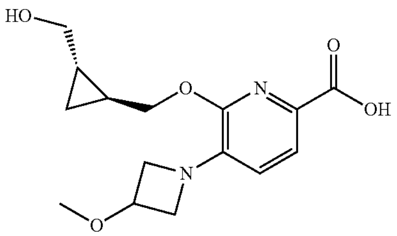 [SMILES: COC1CN(c2ccc(C(=O)O)nc2OC[C@H]2C[C@@H]2CO)C1]

In a 25 mL round bottom flask 6-(((1S,2S)-2-(hydroxymethyl)cyclopropyl) methoxy)-5-(3-methoxyazetidin-1-yl)picolinamide (85 mg, 0.277 mmol, 1 eq.) was dissolved in methanol (3 mL) and water (5 mL). Sodium hydroxide (55 mg, 1.38 mmol, 5 eq.) was added. The reaction mixture was heated to 85° C. for 12 h upon stirring, poured onto water (10 mL) and 1N HCl (3 mL) and extracted with AcOEt (3×20 mL). The combined organic layers were dried over sodium sulfate and concentrated in vacuo. The crude material was purified by flash chromatography ($SiO_2$, 12 g, 40-100% AcOEt in heptane) to give the title compound (64 mg, 0.207 mmol, 75%) as a light orange solid.

$^{1}H$ NMR (600 MHz, $CDCl_3$): δ ppm 7.72 (dd, $^{3}J$=7.9 Hz, $^{4}J$=2.9 Hz, 1H, $N_{Py}$—$C_q$—CH—CH), 6.56 (d, $^{3}J$=7.9 Hz, 1H, $N_{Py}$—$C_q$—CH), 3.99-4.41 (m, 7H, O—$CH_2$, $CH_2$—N—$CH_2$, O—CH, HO—$CH_2$), 3.97-3.99 (m, 2H, $CH_2$—N—$CH_2$), 3.28 (m, 3H, O—$CH_3$), 1.18-1.32 (CH—$CH_2$—CH), 0.56-0.81 (m, 2H, CH—$CH_2$—CH)

HRMS (ESI): $C_{15}H_{20}N_2O_5$ $[M+H]^+$ calculated=309.1379. found=309.1451.

d) 3-Fluoropropyl 2-amino-2-vinylbut-3-enoate

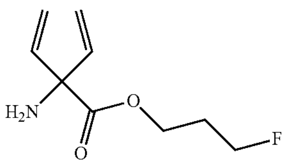

3-Fluoropropan-1-ol (1.55 g, 1.61 mL, 19.8 mmol, Eq.: 18) and 2-amino-2-vinylbut-3-enoic acid hydrochloride (CAN 1865695-91-5, 180 mg, 1.1 mmol, Eq.: 1) were added to a round bottom flask. Sulfurous dichloride (1.31 g, 798 μL, 11 mmol, Eq.: 10) was added. The reaction mixture was stirred for 1 h at 80° C., poured onto water (10 mL) and extracted with $CH_2Cl_2$ (2×20 mL). The organic layers were combined, dried over sodium sulfate, filtered and concentrated in vacuo. The crude material was purified by flash chromatography (silica gel, 12 g, 20% to 70% AcOEt in heptane) to give the title compound as colorless oil, LC-MS (UV peak area/ESI) 94%, 187.1083 $[MH^+]$.

e) 3-Fluoropropyl 2-[[6-[[(1S,2S)-2-(hydroxymethyl)cyclopropyl]methoxy]-5-(3-methoxyazetidin-1-yl)pyridine-2-carbonyl]amino]-2-vinyl-but-3-enoate

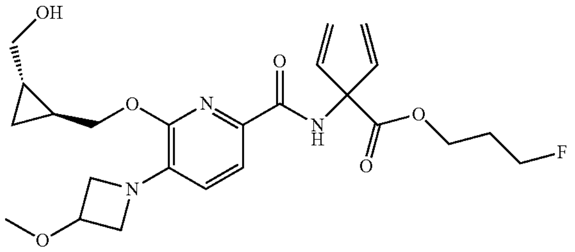 [SMILES: C=CC(C=C)(NC(=O)c1ccc(N2CC(OC)C2)c(OC[C@H]2C[C@@H]2CO)n1)C(=O)OCCCF]

6-(((1S,2S)-2-(Hydroxymethyl)cyclopropyl)methoxy)-5-(3-methoxyazetidin-1-yl)picolinic acid (19.8 mg, 64.1 μmol, Eq.: 0.8) and 3-fluoropropyl 2-amino-2-vinylbut-3-enoate (15 mg, 80.1 μmol, Eq.: 1) were dissolved in $CH_2Cl_2$ (1.34 mL). N-Ethyl-N-isopropylpropan-2-amine (41.4 mg, 55.2 μL, 320 μmol, Eq.: 4) followed by 1-(bis(dimethylamino)methylene)-1H-[1,2,3]triazolo[4,5-b]pyridine-1-ium 3-oxide hexafluorophosphate(V) (36.6 mg, 96.1 μmol, Eq.: 1.2) were added. The reaction mixture was stirred for 1 h at ambient temperature, poured onto water (10 mL) and extracted with $CH_2Cl_2$ (4×20 mL). The organic layers were combined, dried over sodium sulfate, filtered and concentrated in vacuo. The crude material was purified by flash chromatography (silica gel, 12 g, 20% to 70% AcOEt in heptane) to give the title compound as colorless oil, LC-MS (UV peak area/ESI) 98%, 478.2399 $[MH^+]$.

f) 3-Fluoropropyl 2-(1,2-ditritioethyl)-2-[[6-[[(1S, 2S)-2-(hydroxymethyl)cyclopropyl]methoxy]-5-(3-methoxyazetidin-1-yl)pyridine-2-carbonyl]amino]-3, 4-ditritio-butanoate In a 2 ml trituration flask, 3-Fluoropropyl 2-[[6-[[(1S,2S)-2-(hydroxymethyl) cyclopropyl]methoxy]-5-(3-methoxyazetidin-1-yl)pyridine-2-carbonyl]amino]-2-vinyl-but-3-enoate (2.0 mg, 4.2 μmol, 1.0 eq.) and Pd/C (10%) (0.89 mg, 0.84 μmol, 0.2 eq.) were suspended in dimethylformamide (0.4 ml). The flask was attached to the tritium manifold (RC-TRITEC) and degassed by freeze-pump-thaw. Tritium gas was introduced, and the black suspension was vigorously stirred for 3 hours under an atmosphere of tritium at 560 mbar. The solution was cooled by liquid nitrogen and the excess tritium gas in the reaction vessel was reabsorbed on a uranium-trap for waste-tritium. The solvent was lyophilized off and labile tritium was removed by lyophilization with a methanol (3×1 ml). The remaining black residue was suspended in methanol (10 ml) and filtered over a 17 mm Titan HPLC filter (0.45 μm, PTFE) to provide 8.21 GBq (222 mCi) of a crude product in a purity of >90%. The crude product was concentrated and purified by preparative HPLC (SunFire C18, 5 μm, 4.6×250 mm) using acetonitrile [A] and 5% acetonitrile in water [B] as eluent (gradient: 10% [A], 90% [B] to 99% [A], 1% [B] in 12 min, hold for 3 min, then back to initial conditions for 5 min). 4.59 GBq (124 mCi) were obtained of the title compound with a radiochemical purity of 98.7% and a specific activity of 4.18 TBq/mmol (113 Ci/mmol), determined by MS spectrometry. The compound was stored as an ethanolic solution. MS m/z: 482.3 $[M+H]^+$ (1%), 484.3 $[M(^3H)+H]^+$ (5%), 486.3 $[M(^3H_2)+H]^+$ (13%), 488.3 $[M(^3H_3)+H]^+$ (21%), 490.3 $[M(^3H_4)+H]^+$ (12%), 492.3$[M(^3H_5)+H]^+$ (20%), 494.3 $[M(^3H_6)+H]^+$ (12%), 496.3 $[M(^3H_7)+H]^+$ (4%).

Example 4

Radioligand Binding Assay and Micro PET Studies

Stably transfected cells or spleen tissue were homogenized in 15 mmol L-1 Hepes, 0.3 mmol L-1 EDTA, 1 mmol L-1 EGTA, 2 mmol L-1 MgCl2, complete EDTA-free protease inhibitor (Roche Applied Science, Rotkreuz, Switzerland), pH 7.4 using a glass potter and centrifugation at 47,800 g at 4° C. for 30 min. The pellet was then rehomogenized twice in the same buffer and centrifuged (47,800 g, 4° C., 30 min). The final pellet was then resuspended in 75 mmol L-1 Tris, 0.3 mmol L-1 EDTA, 1 mmol L-1 EGTA, 12.5 mmol L-1 MgCl2, 250 mmol L-1 sucrose, pH 7.4 at a protein concentration of 1 to 3 mg mL-1, aliquoted, frozen on dry ice and stored at −80° C.

Saturation binding was performed with 0.05 to 2.4 nM compound of formula (I) and 40 μg of membrane protein. CP55940 (10 μM) was used to define nonspecific binding. Assay buffer consisted of 50 mmol L-1 Tris-HCl, 5 mmol L-1 MgCl2, 2.5 mmol L-1 EGTA, and 0.1% fatty acid-free BSA, pH 7.4. Assays were initiated by addition of membranes in a final volume of 250 μl/well. Assays were incubated for 2 h at room temperature and then vacuum filtered and rinsed with wash buffer (50 mmol L-1 Tris-HCl, 5 mmol L-1 MgCl2, 2.5 mmol L-1 EGTA, and 0.5% fatty acid-free BSA, pH 7.4) on a Filtermate cell harvester through Packard GF/B filters presoaked in 0.3% polyethylenimine.

For competition binding, membrane preparations were incubated either with 0.3 nM of $[^3H]$-CP55940 in the presence or absence of increasing concentrations of unlabeled ($R^1$=$R^2$=$CH_2CH_3$, $R^3$=$CH_2CH_2CH_2F$) compound of formula (I) or with 1.5 nM compound of formula (I) (($R^1$=$R^2$=$CHTCH_2T$, $R^3$=$CH_2CH_2CH_2F$)) and increasing amounts of membranes (2.5-80 μg) in the presence or absence of CP55940 (10 μM) for 60 min at 30° C. in a final volume of 0.2 mL of 50 mmol L-1 Tris-HCl, 5 mmol L-1 MgCl2, 2.5 mmol L-1 EGTA, 0.1% fatty acid-free BSA and 1% DMSO, pH 7.4, buffer, gently shaking. All binding reactions were terminated by vacuum filtration onto 0.5% polyethylenimine presoaked GF/B filter plates (Packard) followed by seven brief washes with 2 mL of ice-cold binding buffer containing 0.5% fatty acid-free BSA. Plates were dried at 50° C. for 1 h and liquid scintillation counting was used to determine bound radiolabel. IC50 values and Hill slopes were determined by a four parameter logistic model using ActivityBase (ID Business Solution, Ltd.).

The results are shown in Table 1 and FIG. 1.

TABLE 1

| Radioligand competition binding of $[^3H]$CP55940 using CHO-K1 cell expressing human CB2 receptors | | |
|---|---|---|
| | Human CB1 | Human CB2 |
| Ki [nM] | >10'000 | 0.7 |

Table 1 demonstrates high binding selectivity of unlabeled compound of formula (I) for human CB2 receptors (Ki 0.7 nM) vs human CB1 receptors (Ki>10,000 nM) in cells that recombinantly express these receptors and using the non-selective CB1/CB2 radioligand $[^3H]$CP55940.

The invention claimed is:

1. A method of imaging a CB2 receptor in a patient or a sample comprising:

(a) administering to said patient or contacting the sample with a compound of formula (I):

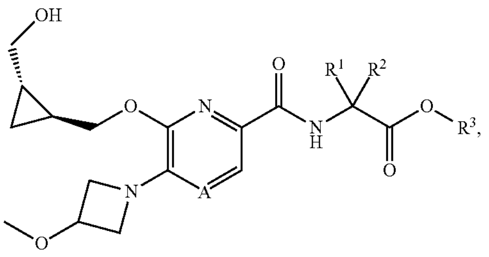

(I)

or a pharmaceutically acceptable salt thereof, wherein:

A is CH;

$R^1$ and $R^2$ are both ethyl at the same time; and $R^3$ is fluoropropyl or hexadeuteriofluoropropyl;

provided that at least one of $R^1$, $R^2$ and $R^3$ comprises at least one positron-emitting radionuclide; and (b) imaging the compound in the patient or in the sample using positron emission tomography (PET) or single-photon emission computed tomography (SPECT).

2. The method of claim 1, wherein the positron emission tomography (PET) is used for imaging.

3. The method of claim 2, wherein in the compound of formula (I) both $R^1$ and $R^2$ comprise at least one radionuclide or $R^3$ comprises a radionuclide.

4. The method of claim 2, wherein in the compound of formula (I) at least one radionuclide is $^{18}F$ or $^{11}C$.

5. The method of claim 4, wherein in the compound of formula (I) $R^3$ is $-CH_2-CH_2-CH_2{}^{18}F$ or $-CD_2-CD_2-CD_2{}^{18}F$.

6. The method of claim 4, wherein the compound of formula (I) is selected from:

3-($^{18}$F) Fluoropropyl 2-ethyl-2-[[6-[[(1S,2S)-2-(hydroxymethyl)cyclopropyl]methoxy]-5-(3-methoxyazetidin-1-yl)pyridine-2-carbonyl]amino]butanoate and (1,1,2,2,3,3-Hexadeuterio-3-($^{18}$F) fluoropropyl) 2-ethyl-2-[[6-[[(1S,2S)-2-(hydroxymethyl)cyclopropyl] methoxy]-5-(3-methoxyazetidin-1-yl)pyridine-2-carbonyl]amino]butanoate or a pharmaceutically acceptable salt thereof.

7. The method of claim 1, wherein the compound is:

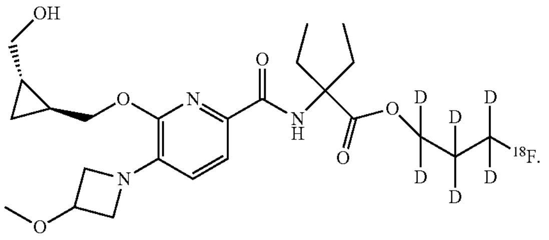

8. A method of imaging a CB2 receptor in a patient or a sample comprising:

(a) administering to said patient or contacting the sample with a compound having the structure:

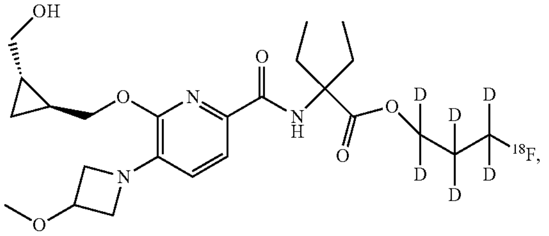

and (b) imaging the compound in the patient or in the sample using positron emission tomography (PET) or single-photon emission computed tomography (SPECT).

9. The method of claim 8, wherein the positron emission tomography (PET) is used for imaging.

10. The method of claim 8, wherein the single-photon emission computed tomography (SPECT) is used for imaging.

* * * * *